(12) United States Patent
Noda (10) Patent No.: US 11,857,929 B2
(45) Date of Patent: Jan. 2, 2024

(54) SUPPORT, ZEOLITE MEMBRANE COMPLEX, METHOD OF PRODUCING ZEOLITE MEMBRANE COMPLEX, AND SEPARATION METHOD

(71) Applicant: NGK INSULATORS, LTD., Nagoya (JP)

(72) Inventor: Kenichi Noda, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 445 days.

(21) Appl. No.: 17/201,269

(22) Filed: Mar. 15, 2021

(65) Prior Publication Data

US 2021/0197136 A1  Jul. 1, 2021

Related U.S. Application Data

(63) Continuation of application No. PCT/JP2019/030538, filed on Aug. 2, 2019.

(30) Foreign Application Priority Data

Sep. 28, 2018  (JP) ................ 2018-183966

(51) Int. Cl.
   *B01D 69/10*  (2006.01)
   *B01D 53/22*  (2006.01)
   (Continued)

(52) U.S. Cl.
   CPC ........... *B01D 69/10* (2013.01); *B01D 53/228* (2013.01); *B01D 67/0051* (2013.01);
   (Continued)

(58) Field of Classification Search
   None
   See application file for complete search history.

(56) References Cited

U.S. PATENT DOCUMENTS

2006/0237360 A1* 10/2006 Mizuno ............. B01D 67/0051
                                                         210/500.21
2009/0011926 A1  1/2009 Yajima et al.
(Continued)

FOREIGN PATENT DOCUMENTS

JP  H09-071481 A1  3/1997
JP  2006-231123 A1  9/2006
(Continued)

OTHER PUBLICATIONS

International Search Report and Written Opinion (Application No. PCT/JP2019/030538) dated Oct. 8, 2019.
(Continued)

*Primary Examiner* — Tam M Nguyen
(74) *Attorney, Agent, or Firm* — BURR PATENT LAW, PLLC (57) ABSTRACT

A porous cylindrical support for use in supporting a zeolite membrane has a generally cylindrical inside surface having a central axis extending in the longitudinal direction and a generally cylindrical outside surface that surrounds the inside surface. A zeolite membrane is formed on the outside surface. A maximum value A and a minimum value B of a support thickness in a circumferential direction satisfy $(A-B)/(A+B) \leq 0.3$ in at least part of the support in the longitudinal direction, the support thickness being a radial distance between the inside surface and the outside surface. By reducing a variation in support thickness, it is possible to improve uniformity in the thickness of the zeolite membrane formed on the support.

5 Claims, 4 Drawing Sheets

(51) Int. Cl.
*B01D 67/00* (2006.01)
*B01D 69/02* (2006.01)
*B01D 69/04* (2006.01)
*B01D 71/02* (2006.01)
*C01B 39/48* (2006.01)
*C07C 7/144* (2006.01)

(52) U.S. Cl.
CPC ............ *B01D 69/02* (2013.01); *B01D 69/04* (2013.01); *B01D 71/028* (2013.01); *C01B 39/48* (2013.01); *C07C 7/144* (2013.01); *B01D 2053/223* (2013.01); *B01D 2325/04* (2013.01)

(56) References Cited

U.S. PATENT DOCUMENTS

| | | | |
|---|---|---|---|
| 2009/0269276 A1 | 10/2009 | Chida et al. | |
| 2010/0071559 A1* | 3/2010 | Miachon | B01D 69/141 96/135 |
| 2017/0189862 A1* | 7/2017 | Imasaka | B01J 20/3238 |
| 2017/0232401 A1* | 8/2017 | Miyahara | B01D 65/003 96/10 |
| 2017/0259214 A1* | 9/2017 | Onozuka | B01D 71/028 |
| 2020/0001199 A1* | 1/2020 | Hidaka | B01D 3/38 |
| 2021/0275975 A1* | 9/2021 | Miyahara | B01D 67/0051 |
| 2022/0297065 A1* | 9/2022 | Kida | C02F 1/44 |
| 2023/0018523 A1* | 1/2023 | Shimizu | C01B 39/02 |
| 2023/0114715 A1* | 4/2023 | Ogasawara | B01D 53/228 585/818 |

FOREIGN PATENT DOCUMENTS

| | | |
|---|---|---|
| JP | 2007-090233 A1 | 4/2007 |
| JP | 2012-066241 A1 | 4/2012 |
| WO | 2007/105407 A1 | 9/2007 |

OTHER PUBLICATIONS

English translation of the International Preliminary Report on Patentability (Chapter I) (Application No. PCT/JP2019/030538) dated Apr. 8, 2021.

* cited by examiner

SUPPORT, ZEOLITE MEMBRANE COMPLEX, METHOD OF PRODUCING ZEOLITE MEMBRANE COMPLEX, AND SEPARATION METHOD

CROSS-REFERENCE TO RELATED APPLICATION

The present application is a continuation application of International Application No. PCT/JP2019/030538, filed on Aug. 2, 2019. The contents of this application are incorporated herein by reference in their entirety.

TECHNICAL FIELD

The present invention relates to a support used to support a zeolite membrane, a zeolite membrane complex including the support, a method of producing the zeolite membrane complex, and a method of separating a mixture of substances with use of the zeolite membrane complex.

BACKGROUND ART

Various studies and developments are currently underway on forming a zeolite membrane on a porous support to obtain a zeolite membrane complex and using the molecular-sieving function of the zeolite in applications such as the separation of specific molecules and the adsorption of specific molecules.

For example, Japanese Patent Application Laid-Open No. H09-71481 (Document 1) discloses a ceramic support that is used as a support of a zeolite membrane. Japanese Patent Application Laid-Open No. 2012-66241 (Document 2) and International Patent Publication WO/2007/105407 (Document 3) disclose zeolite membrane complexes in which a zeolite membrane is formed by hydrothermal synthesis on the outside surface of a cylindrical (tubular) ceramic support.

In general, a cylindrical ceramic support (hereinafter, simply referred to as a "support") is produced by extrusion molding and surface grinding. Specifically, first, green body prepared by kneading a predetermined raw material is supplied to and extruded from a mold while being molded into a cylindrical form. Then, a generally cylindrical compact extruded from the mold is fired, and thereafter the outside surface of the fired compact is grinded so as to have an almost perfect circular shape in cross section. This forms the aforementioned support.

In the preparation of this cylindrical support, the support may have a varying radial thickness in the circumferential direction due to factors such as a variation in the rate of supply of the green body to the mold. The variation in the radial thickness of the support may also be caused by other factors such as imbalances in the amount of grinding during grinding of the outside surface. Specifically, when a cylindrical compact is extruded from the mold, the cylindrical compact may extend laterally by gravity so as to have inside and outside surfaces that have generally horizontally-long-elliptical shapes in cross section. In this case, the amount by which the lateral sides of the support are grinded becomes greater than the amount by which the vertical sides of the support are grinded, in order to make the cross-sectional shape of the outside surface close to a perfect circle. As a result, the support is made to a smaller lateral thickness than the vertical thickness.

If a zeolite membrane is formed on a cylindrical support having such a varying thickness, variations will increase in the amount of seed crystals supplied per unit area to the surface of the support, and accordingly uniformity will decrease in the membrane thickness of the zeolite membrane. It is thus difficult to form a dense and thin zeolite membrane with high yields. However, no studies have been made from the viewpoint of the degree to which it is necessary to suppress variations in the thickness of a support in order to form a dense and thin zeolite membrane.

SUMMARY OF INVENTION

The present invention is directed to a porous cylindrical support that is used to support a zeolite membrane. A support according to a preferable embodiment of the present invention includes a generally cylindrical inside surface having a central axis extending in a longitudinal direction and a generally cylindrical outside surface that surrounds the inside surface. A maximum value A and a minimum value B of a support thickness in a circumferential direction satisfy $(A-B)/(A+B) \leq 0.3$ in at least part of the support in the longitudinal direction, the support thickness being a radial distance between the inside surface and the outside surface. Accordingly, it is possible to improve uniformity in the membrane thickness of the zeolite membrane.

Preferably, the maximum value A and the minimum value B satisfy $(A-B)/(A+B) \leq 0.3$ along an entire length of the support in the longitudinal direction.

Preferably, the maximum value A and the minimum value B satisfy $(A-B)/(A+B) \leq 0.2$ in at least part of the support in the longitudinal direction.

Preferably, the inside surface has a mean radius X and roundness Y that satisfy $Y/X \leq 0.5$ in the at least part of the support in the longitudinal direction.

Preferably, the support is formed of a ceramic sintered compact.

The present invention is also directed to a zeolite membrane complex. A zeolite membrane complex according to a preferable embodiment of the present invention includes the aforementioned support and a zeolite membrane formed on the support.

Preferably, a maximum number of membered rings in a zeolite of the zeolite membrane is less than or equal to 8.

Preferably, the zeolite membrane has a thickness less than or equal to 1 μm.

The present invention is also directed to a method of producing a zeolite membrane complex. A method of producing a zeolite membrane complex according to a preferable embodiment of the present invention includes a) preparing seed crystals, b) depositing the seed crystals on the aforementioned support, and c) forming a zeolite membrane on the support by growing a zeolite from the seed crystals by hydrothermal synthesis.

The present invention is also directed to a separation method. A separation method according to a preferable embodiment of the present invention includes d) preparing the aforementioned zeolite membrane complex, and e) supplying a mixture of substances that includes a plurality of types of gases or liquids to the zeolite membrane complex and separating a high-permeability substance in the mixture of substances from the mixture of substances by causing the high-permeability substance to permeate through the zeolite membrane complex.

Preferably, the mixture of substances includes one or more kinds of substances including hydrogen, helium, nitrogen, oxygen, water, water vapor, carbon monoxide, carbon dioxide, nitrogen oxide, ammonia, sulfur oxide, hydrogen sulfide, sulfur fluoride, mercury, arsine, hydrocyanic acid, carbonyl sulfide, C1 to C8 hydrocarbons, organic acid, alcohol, mercaptans, ester, ether, ketone, and aldehyde.

These and other objects, features, aspects and advantages of the present invention will become more apparent from the following detailed description of the present invention when taken in conjunction with the accompanying drawings.

DESCRIPTION OF EMBODIMENTS

Figure 1:
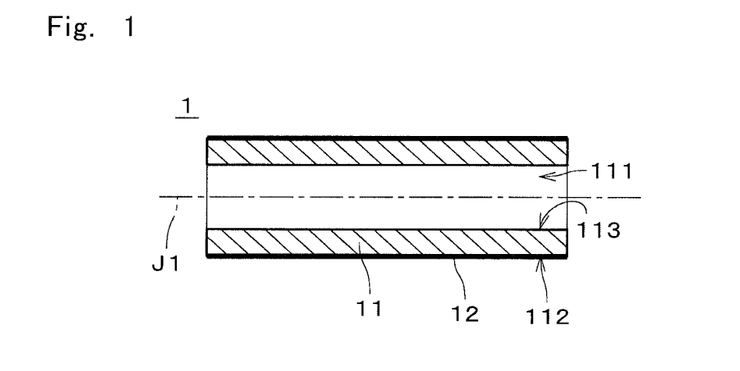
FIG. 1 is a sectional view of a zeolite membrane complex.
Figure 2:
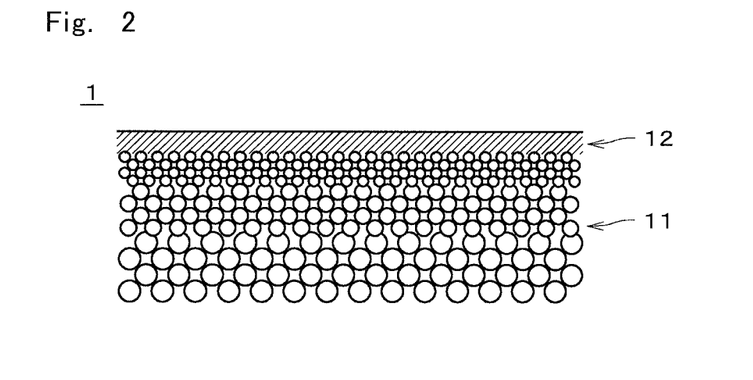
FIG. 2 is an enlarged sectional view of the zeolite membrane complex.

FIG. 1 is a sectional view of a zeolite membrane complex 1. FIG. 2 is a sectional view illustrating part of the zeolite membrane complex 1 in enlarged dimension. The zeolite membrane complex 1 includes a porous support 11 and a zeolite membrane 12 formed on the support 11. In FIG. 1, the zeolite membrane 12 is illustrated with bold lines. In FIG. 2, the zeolite membrane 12 is cross-hatched. The membrane thickness of the zeolite membrane 12 illustrated in FIG. 2 is thicker than the actual membrane thickness.

The support 11 is a cylindrical member. The support 11 is a porous member that is permeable to gases and liquids. The support 11 has an inside surface 113 that is generally cylindrical about a central axis J1 extending in a longitudinal direction (i.e., a right-left direction in FIG. 1), and an outside surface 112 that is generally cylindrical and surrounds the inside surface 113. The central axis J1 as used herein refers to a central axis of a virtual cylinder arranged so as to circumscribe the inside surface 113. The outside surface 112 is located outward of the inside surface 113 in a radial direction about the central axis J1 (hereinafter, also simply referred to as the "radial direction") and surrounds the inside surface 113. The outside surface 112 has the zeolite membrane 12 formed thereon. The zeolite membrane 12 covers approximately the entire outside surface 112 of the support 11. In the following description, a generally columnar space located radially inward of the inside surface 113 is referred to as an "inner flow path 111."

The support 11 has a length (i.e., length in the right-left direction in FIG. 1) of, for example, 10 cm to 200 cm. The support 11 has an outer diameter of, for example, 0.5 cm to 30 cm. A distance in the radial direction between the inside surface 113 and the outside surface 112 of the support 11 (hereinafter, also referred to as a "support thickness") is, for example, in the range of 0.1 mm to 10 mm. Surface roughness (Ra) of the support 11 is, for example, in the range of 0.1 μm to 5.0 μm and preferably in the range of 0.2 μm to 2.0 μm.

As the material for the support 11, various substances (e.g., ceramic or metal) may be employed as long as they are chemically stable during the step of forming the zeolite membrane 12 on the surface of the support 11. In the present embodiment, the support 11 is formed of a ceramic sintered compact. Examples of the ceramic sintered compact that is selected as the material for the support 11 include alumina, silica, mullite, zirconia, titania, yttrium, silicon nitride, and silicon carbide. In the present embodiment, the support 11 contains at least one of alumina, silica, and mullite.

The support 11 may contain an inorganic binder. The inorganic binder may be at least one of titania, mullite, easily sinterable alumina, silica, glass frit, clay minerals, and easily sinterable cordierite.

A mean particle diameter of the support 11 in the vicinity of the surface where the zeolite membrane 12 is formed is smaller than a mean particle diameter of the support 11 in the other portions. To achieve this structure, the support 11 has a multilayer structure. When the support 11 has a multilayer structure, the material for each layer may be any of the materials described above, and each layer may be formed of the same material or may be formed of a different material. The mean pore diameter of the support 11 can be measured using an apparatus such as a mercury porosimeter, a perm porometer, or a nano-perm porometer.

The mean pore diameter of the support 11 is, for example, in the range of 0.01 μm to 70 μm and preferably in the range of 0.05 μm to 25 μm. In a pore size distribution of the support 11 in the vicinity of the surface where the zeolite membrane 12 is formed, D5 is, for example, in the range of 0.01 μm to 50 μm, D50 is, for example, in the range of 0.05 μm to 70 μm, and D95 is, for example, in the range of 0.1 μm to 2000 μm. A porosity of the support 11 in the vicinity of the surface where the zeolite membrane 12 is formed is, for example, in the range of 25% to 50%.

Figure 3:
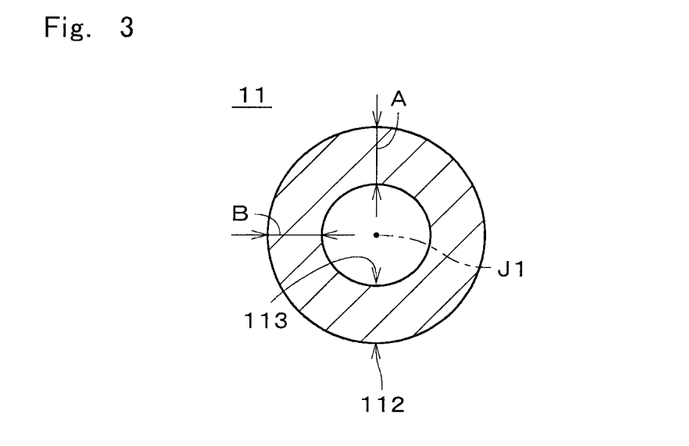
FIG. 3 is a sectional view of a support.

FIG. 3 is a diagram illustrating a section of the support 11 that is perpendicular to the longitudinal direction (i.e., section perpendicular to the central axis J1). In FIG. 3, a position at which the distance in the radial direction between the inside surface 113 and the outside surface 112 of the support 11 becomes a maximum is indicated by arrows, and the support thickness at this position is assumed to be a maximum value A of the support thickness. A position at which the distance in the radial direction between the inside surface 113 and the outside surface 112 of the support 11 becomes a minimum is also indicated by arrows, and the support thickness at this position is assumed to be a minimum value B of the support thickness.

The maximum value A and the minimum value B of the support thickness in one cross-section of the support 11, which is perpendicular to the central axis J1, satisfy "(A−B)/(A+B)≤0.3." In other words, this relation between the maximum value A and the minimum value B is satisfied in at least part of the support 11 in the longitudinal direction. Preferably, this relation between the maximum value A and the minimum value B is satisfied along the entire length of the support 11 in the longitudinal direction (i.e., in each cross-section in the longitudinal direction).

Preferably, the maximum value A and the minimum value B of the support thickness satisfy (A−B)/(A+B)≤0.2 in at least part of the support 11 in the longitudinal direction. More preferably, this relation between the maximum value A and the minimum value B of the support thickness is satisfied along the entire length of the support 11 in the longitudinal direction (i.e., in each cross-section in the longitudinal direction).

A mean radius X and roundness Y of the inside surface 113 of the support 11 in the above one cross-section perpendicular to the central axis J1 satisfy Y/X≤0.5. In other words, this relation between the mean radius X and the roundness Y is satisfied in at least part of the support 11 in the longitudinal direction. Preferably, this relation between the mean radius X and the roundness Y is satisfied along the entire length of the support 11 in the longitudinal direction (i.e., in each cross-section in the longitudinal direction). The mean radius X in one cross-section of the support 11 is an arithmetical mean of the maximum radius and the minimum radius in this cross-section. The roundness Y is obtained in conformity with JIS-B-0621. Specifically, in this cross-section, a rough circle (i.e., circular form) serving as the inside surface 113 is sandwiched between two concentric geometric circles, and a difference between the radii of these two geometric circles, obtained when the interval between the two geometric circles becomes a minimum, is regarded as the roundness Y.

The zeolite membrane 12 is a porous membrane with small pores. The zeolite membrane 12 can be used as a separation membrane that separates a specific substance from a mixture of substances including a plurality of types of substances, using its molecular sieving function. The zeolite membrane 12 is less permeable to the other substances than to the specific substance. In other words, a permeance of the other substances through the zeolite membrane 12 is lower than a permeance of the above specific substance through the zeolite membrane 12.

The zeolite membrane 12 has a membrane thickness of, for example, 0.05 μm to 30 μm, preferably 0.1 μm to 20 μm, and more preferably 0.5 μm to 10 μm. The membrane thickness of the zeolite membrane 12 as used herein refers to a minimum value for the distance from the surface of the support 11 to the surface of the zeolite membrane 12 (i.e., minimum thickness) in the overall zeolite membrane 12 with the exception of defective portions. The same also applies to the following description. In the present embodiment, the membrane thickness of the zeolite membrane 12 is less than or equal to 1 μm. A mean membrane thickness of the zeolite membrane 12 is preferably less than or equal to 5 μm, more preferably less than or equal to 3 μm, and yet more preferably less than or equal to 2 μm. Increasing the membrane thickness of the zeolite membrane 12 improves the selectivity. Reducing the thickness of the zeolite membrane 12 increases the permeance. Surface roughness (Ra) of the zeolite membrane 12 is, for example, less than or equal to 5 μm, preferably less than or equal to 2 m, and more preferably less than or equal to 1 μm. Yet more preferably, the surface roughness (Ra) of the zeolite membrane 12 is less than or equal to 0.5 μm Examples of the zeolite of the zeolite membrane 12 include a zeolite in which atoms (T atoms) located in the center of an oxygen tetrahedron ($TO_4$) constituting the zeolite are composed of only Si or composed of Si and Al, an AlPO-type zeolite in which the T atoms are composed of Al and P, an SAPO-type zeolite in which the T atoms are composed of Si, Al, and P, an MAPSO-type zeolite in which the T atoms are composed of magnesium (Mg), Si, Al, and P, and a ZnAPSO zeolite in which the T atoms are composed of zinc (Zn), Si, Al, and P. Some of the T atoms may be replaced by other elements.

When n represents a maximum number of membered rings in the zeolite of the zeolite membrane 12, an arithmetical mean of the major and minor axes of an n-membered ring pore is assumed to be a mean pore diameter. The n-membered ring pore as used herein refers to a pore whose number of oxygen atoms that are bonded to T atoms and make a ring structure is n. When the zeolite has a plurality of n-membered ring pores where n is the same number, an arithmetical mean of the major and minor axes of all n-numbered rings is assumed to be the mean pore diameter of the zeolite. In this way, the mean pore diameter of the zeolite membrane is uniquely determined by the framework structure of the zeolite and can be obtained from a value disclosed in "Database of Zeolite Structures" [online] by the International Zeolite Association on the Internet <URL: http://www.iza-structure. org/databases/>.

The mean particle diameter of the zeolite membrane 12 is preferably greater than or equal to 0.2 nm and less than or equal to 0.8 nm, more preferably greater than or equal to 0.3 nm and less than or equal to 0.6 nm, and yet more preferably greater than or equal to 0.3 nm and less than or equal to 0.5 nm. The mean particle diameter of the zeolite membrane 12 is smaller than the mean pore diameter of the support 11 in the vicinity of the surface where the zeolite membrane 12 is formed.

There are no particular limitations on the type of the zeolite of the zeolite membrane 12, but from the viewpoint of increasing the $CO_2$ flux and improving the $CO_2$ selectivity, a maximum number of atoms in the ring of the zeolite is preferably less than or equal to 8 (e.g., 6 or 8). The zeolite membrane 12 is, for example, a DDR-type zeolite. In other words, the zeolite membrane 12 is a zeolite membrane composed of a zeolite having a framework type code "DDR" assigned by the International Zeolite Association. In this case, the zeolite of the zeolite membrane 12 has an intrinsic pore diameter of 0.36 nm×0.44 nm and a mean pore diameter of 0.40 nm.

For example, the zeolite membrane 12 may be any of the following types including AEI-type, AEN-type, AFN-type, AFV-type, AFX-type, BEA-type, CHA-type, ERI-type, ETL-type, FAU-type (X-type, Y-type), GIS-type, LEV-type, LTA-type, MEL-type, MFI-type, MOR-type, PAU-type, RHO-type, SAT-type, and SOD-type.

The zeolite membrane 12 contains, for example, silicon (Si). For example, the zeolite membrane 12 may contain any two or more of Si, aluminum (Al), and phosphorus (P). The zeolite membrane 12 may contain alkali metal. The alkali metal is, for example, sodium (Na) or potassium (K). When the zeolite membrane 12 contains Si atoms, an Si/Al ratio in the zeolite membrane 12 is, for example, higher than or equal to 1 and lower than or equal to 100,000. The Si/Al ratio is preferably higher than or equal to 5, more preferably higher than or equal to 20, and yet more preferably higher than or equal to 100. This ratio is preferably as high as possible. The Si/Al ratio in the zeolite membrane 12 can be adjusted by, for example, adjusting the composition ratio of an Si source and an Al source in a starting material solution, which will be described later.

Figure 4:
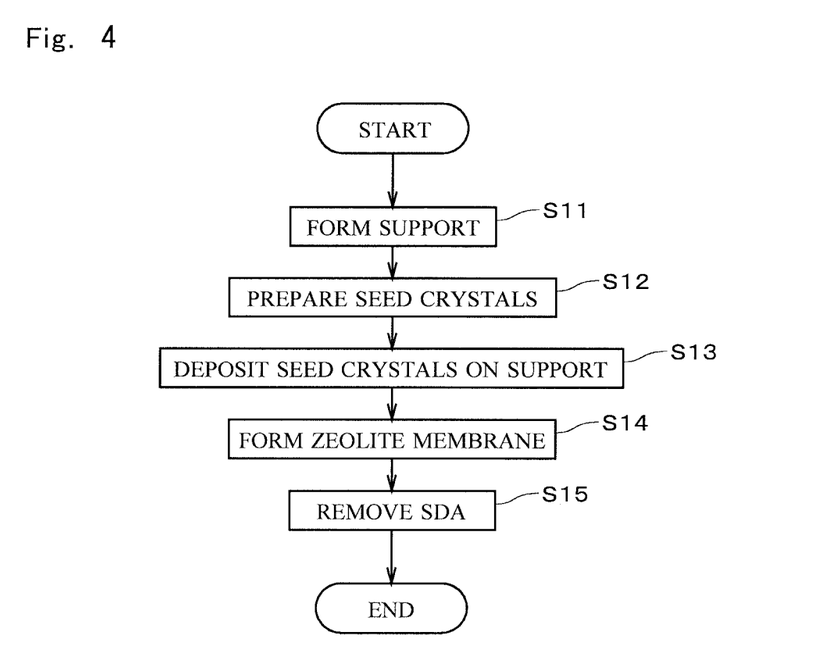
FIG. 4 is a diagram illustrating a procedure for producing the zeolite membrane complex.

Next, one example of the procedure for producing the zeolite membrane complex 1 will be described with reference to FIG. 4. In the production of the zeolite membrane complex 1, first, the support 11 is formed (step S11). Specifically, first, green body that is a material for the support 11 is prepared by kneading ceramic particles, an inorganic binder, water, a dispersant, and a thickener. Then, the green body is subjected to extrusion molding so as to form a generally cylindrical compact. This compact is then fired to obtain a generally cylindrical fired compact. Then, the outside surface of the fired compact is grinded into a support member. Thereafter, a porous ceramic membrane that has smaller pore diameters than the pore diameters of the support member is formed as an intermediate layer on the outside surface of the support member, and another porous ceramic membrane that has yet smaller pore diameters is formed as a surface layer on the intermediate layer. In this way, the support 11 having a multilayer structure is formed.

In the aforementioned preparation of the green body, for example, 0.1 to 50 parts by mass (in the present embodiment, 20 parts by mass) of the inorganic binder is added to 100 parts by mass of the ceramic particles (in the present embodiment, alumina particles). The alumina particles have a mean particle diameter of, for example, 1 μm to 200 μm and in the present embodiment, 50 μm. A firing temperature of the aforementioned compact is in the range of, for example, 1000° C. to 1800° C., and in the present embodiment, 1250° C. A firing time of the aforementioned compact is, for example, in the range of 0.1 to 100 hours, and in the present embodiment, one hour.

For example, the outside surface of the fired compact is grinded with a belt-type grinder by a belt centerless method using fixed abrasive grains of a diamond grinding wheel. Various modifications may be made to the grinding method and the type of the grinder, used in this grinding. The intermediate layer and the surface layer described above are, for example, porous alumina membranes with thicknesses of several micrometers to several hundred micrometers. The intermediate layer and the surface layer are formed by, for example, vacuum filtration deposition. Alternatively, the intermediate layer and the surface layer may be formed by other methods. The intermediate layer has a mean pore diameter of, for example, 0.1 jam to 10 μm, and in the present embodiment, 0.5 μm. The surface layer has a mean pore diameter of, for example, 0.01 μm to 5 μm, and in the present embodiment, 0.1 μm.

Then, seed crystals that are used to produce the zeolite membrane 12 are prepared (step S12). For example, the seed crystals are acquired from DDR-type zeolite powder synthesized by hydrothermal synthesis. This zeolite powder may be used as-is as seed crystals, or may be processed into seed crystals by pulverization or other methods. Note that step S12 may be performed in parallel with step S11, or may be performed before step S11.

Figure 5:
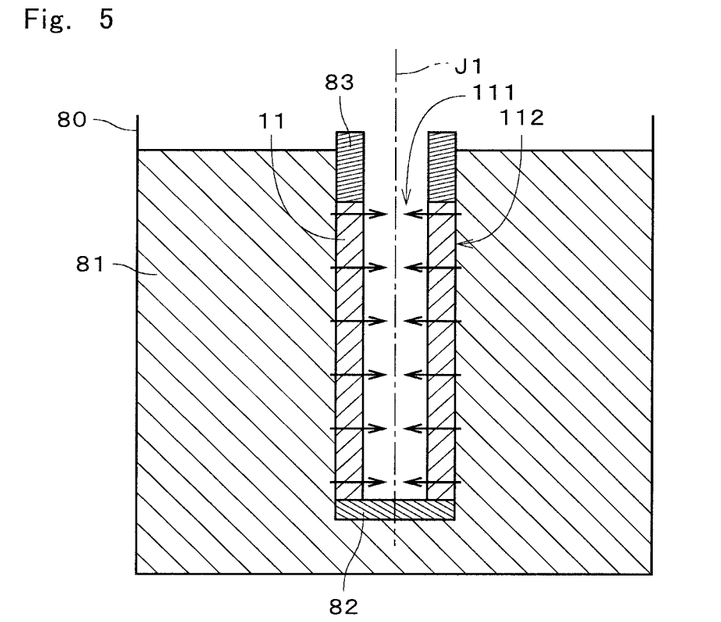
FIG. 5 is a diagram illustrating a zeolite membrane complex in the course of production.

Next, the seed crystals are deposited on the outside surface 112 of the support 11 (step S13). In step S13, for example, the seed crystals are deposited by filtration on the support 11. Specifically, first, the lower-end opening of the support 11 that stands upright with the central axis J1 running parallel to the up-down direction is sealed in a liquid-tight manner, and the upper-end opening thereof is attached in a liquid-tight manner to a generally cylindrical opening member 83 made of a liquid-tight material. Then, as illustrated in FIG. 5, the support 11 is inserted from the lower end side (i.e., the side on which a seal member 82 is attached) into a reservoir 80 that stores a solution 81 in which the seed crystals are dispersed, and is immersed in the solution 81. An upper-end opening of the opening member 83 attached to the upper end of the support 11 is located above the liquid level of the solution 81, and the outside surface 112 of the support 11 is located within the solution 81. Accordingly, a solvent in the solution 81 permeates through the support 11 from the outside surface 112 of the support 11 and moves to the inner flow path 111, as indicated by arrows pointing in the right-left direction in FIG. 5. On the other hand, the seed crystals in the solution 81 remain on and adhere to the outside surface 112 of the support 11 without permeating through the support 11. In this way, a seed-crystal-deposited support is prepared.

When step S13 has ended, the support 11 with the seed crystals deposited thereon is taken out of the solution 81 and dried. The dried support 11 with the seed crystals deposited thereon is immersed in a starting material solution. For example, the starting material solution is prepared by dissolving or dispersing substances such as an Si source and a structure-directing agent (hereinafter, also referred to as an "SDA") in a solvent. The solvent in the starting material solution may be water or alcohol such as ethanol. The SDA contained in the starting material solution may, for example, be an organic compound. For example, 1-adamantanamine may be used as the SDA.

Then, using the seed crystals as nuclei, the DDR-type zeolite is grown by hydrothermal synthesis into the DDR-type zeolite membrane 12 on the support 11 (step S14). The temperature of the hydrothermal synthesis is preferably in the range of 120° C. to 200° C., and for example, 160° C. The time of the hydrothermal synthesis is preferably in the range of 10 hours to 100 hours, and for example, 30 hours.

When the hydrothermal synthesis has ended, the support 11 and the zeolite membrane 12 are rinsed with deionized water. After the rinsing, the support 11 and the zeolite membrane 12 are dried at, for example, 80° C. After the support 11 and the zeolite membrane 12 have been dried, the zeolite membrane 12 is subjected to heat treatment so as to almost completely burn and remove the SDA in the zeolite membrane 12 and cause micropores in the zeolite membrane 12 to come through the membrane (step S15). In this way, the aforementioned zeolite membrane complex 1 is obtained.

In the aforementioned production of the zeolite membrane complex 1, if the support 11 has a greatly varying support thickness, the amount of seed crystals to be deposited in step S13 will also vary. Specifically, a thin portion of the support 11 with a small support thickness has low resistance when the solvent in the above solution permeates through the support 11. This increases the amount of the solvent permeating through the thin portion of the support 11 and also increases the amount of seed crystals deposited on the outside surface 112 of the thin portion of the support 11. On the other hand, a thick portion of the support 11 with a large support thickness has high resistance when the solvent permeates through the support 11. This reduces the amount of the solvent permeating through the thick portion of the support 11 and also reduces the amount of seed crystals deposited on the outside surface 112 of the thick portion of the support 11. As a result, the zeolite membrane 12 increases in thickness in portions of the zeolite membrane complex 1 that have small support thicknesses, and the zeolite membrane 12 decreases in thickness in portions of the zeolite membrane complex that have large support thicknesses. Accordingly, variations occur in the membrane thickness of the zeolite membrane 12.

Table 1 shows the relation of variations in support thickness and variations in the membrane thickness of the zeolite membrane 12 in the zeolite membrane complex 1. Generally cylindrical supports 11 according to Examples 1 to 7 have an outer diameter of 20 mm and a longitudinal length of 15 cm. The same applies to the support according to Comparative Example 1. Zeolite membranes 12 according to Examples 1 to 3 and a zeolite membrane according to Comparative Example 1 are DDR-type zeolite membranes. Zeolite membranes 12 according to Examples 4 and 5 are CHA-type zeolite membranes. Zeolite membranes 12 according to Examples 6 and 7 are AEI-type zeolite membranes.

The zeolite membrane complexes 1 according to Examples 1 to 7 and the zeolite membrane complex according to the comparative example were produced by a production method approximately similar to the production method illustrated in steps S11 to S15 described above. Detailed production conditions and the like will be described below.

For the production of the DDR-type zeolite membranes 12 according to Examples 1 to 3, in step S13, a slurry solution for seed deposition, prepared such that DDR-type zeolite seed crystals dispersed in water had a concentration of 0.1% by mass, was used as the aforementioned solution 81. Then, the support 11 with the seed crystals deposited thereon was subjected to through-circulation drying with predetermined conditions (at room temperature, at an air velocity of 5 m/sec, for 10 minutes). In step S14, 88.0 g of 30% by weight of silica sol (trade name: SNOWTEX S manufactured by Nissan Chemical Corporation), 6.59 g of ethylenediamine (produced by FUJIFILM Wako Pure Chemical Corporation), 1.04 g of 1-adamantanamine (produced by Sigma-Aldrich, Japan), and 104.4 g of deionized water were mixed for preparation of the aforementioned starting material solution. The zeolite membrane 12 was synthesized by hydrothermal synthesis for 10 hours in an oven set at 130° C. The removal of the SDA was implemented by heating the support 11 with the zeolite membrane 12 formed thereon at 450° C. for 50 hours in an electric furnace. The same applies to the production of the DDR-type zeolite membrane according to Comparative Example 1.

For the production of the CHA-type zeolite membranes 12 according to Examples 4 and 5, in step S12, CHA-type zeolite seed crystals were prepared by interzeolite conversion of a Y-type zeolite or by hydrothermal synthesis of an aluminosilicate solution or the like. In step S13, a slurry solution for seed deposition, prepared such that the CHA-type zeolite seed crystals dispersed in water had a concentration of 0.1% by mass, was used as the aforementioned solution 81. Then, the support 11 with the seed crystals deposited thereon was subjected to through-circulation drying conducted with predetermined conditions (at room temperature, at an air velocity of 5 m/sec, for 10 minutes). In step S14, 21.3 g of 30% by weight of silica sol (trade name: SNOWTEX S manufactured by Nissan Chemical Corporation), 0.90 g of potassium hydroxide (produced by FUJIFILM Wako Pure Chemical Corporation), 1.18 g of sodium aluminate (produced by FUJIFILM Wako Pure Chemical Corporation), 3.58 g of 25% by mass of an N, N, N-trimethyl-1-ammonium hydroxide solution (produced by SACHEM, INC.), and 173.1 g of deionized water were mixed for preparation of the aforementioned starting material solution. The zeolite membrane 12 was synthesized by hydrothermal synthesis for 30 hours in an oven set at 160° C. The removal of the SDA was implemented by heating the support 11 having the zeolite membrane 12 formed thereon at 550° C. for 10 hours.

For the production of the AEI-type zeolite membranes 12 according to Examples 6 and 7, in step S12, AEI-type zeolite seed crystals were prepared by hydrothermal synthesis of an aluminophosphate solution or the like. In step S13, a slurry solution for seed deposition, prepared such that the AEI-type zeolite seed crystals dispersed in water had a concentration of 0.1% by mass, was used as the aforementioned solution 81. Then, the support 11 with the seed crystals deposited thereon was subjected to through-circulation drying conducted with predetermined conditions (at room temperature, at an air velocity of 2 m/sec to 7 m/sec, for 30 minutes). In step S13, the application of the slurry solution for seed position and the through-circulation drying were conducted twice. In step S14, 4.72 g of aluminum tri-isopropoxide (produced by KANTO CHEMICAL CO., INC.), 30.71 g of 35% by mass of a tetraethylammonium hydroxide solution (produced by Sigma-Aldrich, Japan), 8.41 g of 85% phosphoric acid (produced by Sigma-Aldrich, Japan), and 156.17 g of deionized water were mixed for preparation of the aforementioned starting material solution. The zeolite membrane 12 was synthesized by hydrothermal synthesis at 150° C. for 30 hours. The removal of the SDA was implemented by heating the support 11 having the zeolite membrane 12 formed thereon at 400° C. for 10 hours.

TABLE 1

| Type of Zeolite Membrane | Variation in Support Thickness (A − B)/(A + B) | Variation in Membrane Thickness $\|a - b\|/((a + b)/2)$ |
| --- | --- | --- |
| Example 1 | DDR-type zeolite membrane | 0.09 | 3% |
| Example 2 | DDR-type zeolite membrane | 0.18 | 4% |
| Example 3 | DDR-type zeolite membrane | 0.28 | 7% |
| Comparative Example 1 | DDR-type zeolite membrane | 0.36 | 14% |
| Example 4 | CHA-type zeolite membrane | 0.09 | 4% |
| Example 5 | CHA-type zeolite membrane | 0.28 | 8% |
| Example 6 | AEI-type zeolite membrane | 0.09 | 4% |
| Example 7 | AEI-type zeolite membrane | 0.28 | 9% |

Variation in support thickness in Table 1 represents "(A−B)/(A+B)" described above in one cross-section of the support 11. That is, the variation in support thickness corresponds to a value obtained by dividing the difference between the maximum value A and minimum value B of the support thickness in one cross-section of the support 11 by the sum of the maximum value A and the minimum value B. The variation in support thickness increases as this value increases.

Variation in membrane thickness in Table 1 represents a value obtained by dividing the absolute value of the difference between membrane thicknesses "a" and "b" by an arithmetical mean of the membrane thicknesses "a" and "b" in the above cross-section of the support 11 (i.e., "|a-b|/((a+b)/2)"), where "a" is the membrane thickness of a given portion of the zeolite membrane 12 where the support thickness is the maximum value A, and "b" is the membrane thickness of a given portion of the zeolite membrane 12 where the support thickness is the minimum value B. In Table 1, this value is expressed in percentage. The variation in the membrane thickness of the zeolite membrane 12 increases as this value increases.

The maximum value A and minimum value B of the support thickness and the membrane thicknesses "a" and "b", described above, were obtained by cutting the support 11 along a plane perpendicular to the central axis J1 and observing the cross section using a scanning electron microscope (SEM).

When the variation in support thickness, i.e., (A−B)/(A+B), is greater than 0.3 as in Comparative Example 1, the variation in the membrane thickness of the DDR-type zeolite membrane 12, i.e., |a-b|/((a+b)/2), is greater than 10%. On the other hand, when the variation in support thickness, i.e., (A−B)/(A+B), is less than or equal to 0.3 as in Examples 1 to 3, the variation in the membrane thickness of the DDR-type zeolite membrane 12, i.e., |a-b|/((a+b)/2), is less than or equal to 10%.

Similarly, with the CHA-type zeolite membrane 12, when the variation in support thickness, i.e., (A−B)/(A+B), is less than or equal to 0.3, the variation in the membrane thickness of the zeolite membrane 12, i.e., |a-b|/((a+b)/2), is less than or equal to 10% (Examples 4 and 5). Similarly, with the AEI-type zeolite membrane 12, when the variation in support thickness, i.e., (A−B)/(A+B), is less than or equal to 0.3, the variation in the membrane thickness of the zeolite membrane 12, i.e., |a-b|/((a+b)/2), is less than or equal to 10% (Examples 6 and 7).

Figure 6:
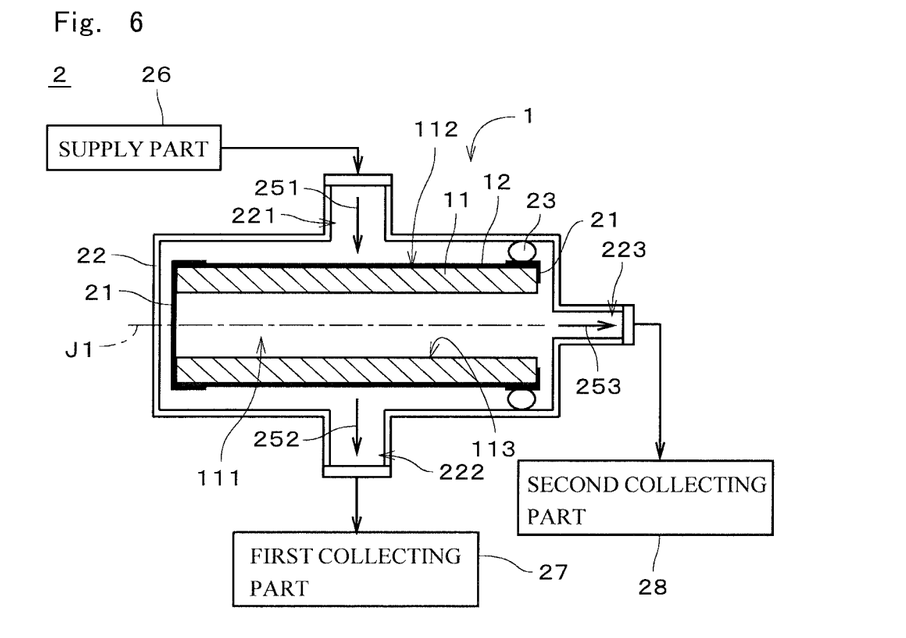
FIG. 6 is a diagram illustrating a separation apparatus.
Figure 7:
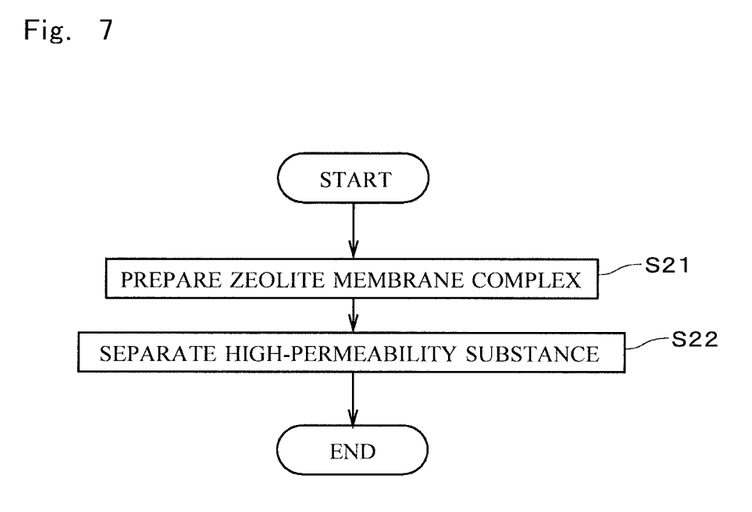
FIG. 7 is a diagram illustrating a procedure for separating a mixture of substances.

Next, the separation of a mixture of substances using the zeolite membrane complex 1 will be described with reference to FIGS. 6 and 7. FIG. 6 is a diagram illustrating a separator 2. FIG. 7 is a diagram illustrating a procedure for separating a mixture of substances, performed by the separator 2.

The separator 2, in which a mixture of substances including a plurality of types of fluids (i.e., gases or liquids) is supplied to the zeolite membrane complex 1, separates a substance having high permeability in the mixture of substances from the mixture of substances by causing the substance to permeate through the zeolite membrane complex 1. For example, the separator 2 may made the separation for the purpose of extracting a substance having high permeability from the mixture of substances, or for the purpose of condensing a substance having low permeability.

The mixture of substances (i.e., mixed fluid) may be a mixed gas including a plurality of types of gases, may be a mixed solution including a plurality of types of liquids, or may be gas-liquid two-phase fluid including both gases and liquids.

In the separator 2, the $CO_2$ permeance of the zeolite membrane complex 1 at temperatures of 20° C. to 400° C. is, for example, greater than or equal to 100 nmol/m$^2$·s·Pa. The ratio (permeance ratio) between the amount of $CO_2$ permeance and the amount of $CH_4$ permeance (leakage) of the zeolite membrane complex 1 at temperatures of 20° C. to 400° C. is, for example, higher than or equal to 100. The permeance and the permeance ratio are values for the case where a difference in the partial pressure of $CO_2$ between the supply side and the permeation side of the zeolite membrane complex 1 is 1.5 MPa.

The mixture of substances includes, for example, one or more kinds of substances including hydrogen ($H_2$), helium (He), nitrogen ($N_2$), oxygen ($O_2$), water ($H_2O$), water vapor ($H_2O$), carbon monoxide (CO), carbon dioxide ($CO_2$), nitrogen oxide, ammonia ($NH_3$), sulfur oxide, hydrogen sulfide ($H_2S$), sulfur fluoride, mercury (Hg), arsine ($AsH_3$), hydrocyanic acid (HCN), carbonyl sulfide (COS), C1 to C8 hydrocarbons, organic acid, alcohol, mercaptans, ester, ether, ketone, and aldehyde.

Nitrogen oxide is a compound of nitrogen and oxygen. The aforementioned nitrogen oxide is, for example, a gas called NOx such as nitrogen monoxides (NO), nitrogen dioxides ($NO_2$), nitrous oxide (also referred to as dinitrogen monoxide) ($N_2O$), dinitrogen trioxide ($N_2O_3$), dinitrogen tetroxide ($N_2O_4$), or dinitrogen pentoxide ($N_2O_5$).

Sulfur oxide is a compound of sulfur and oxygen. The aforementioned sulfur oxide is, for example, a gas called SOx such as sulfur dioxide ($SO_2$) or sulfur trioxide ($SO_3$).

Sulfur fluoride is a compound of fluorine and sulfur. The aforementioned sulfur fluoride may, for example, be disulfur difluoride (F—S—S—F, S=$SF_2$), sulfur difluoride ($SF_2$), sulfur tetrafluoride ($SF_4$), sulfur hexafluoride ($SF_6$), or disulfur decafluoride ($S_2F_{10}$).

C1 to C8 hydrocarbons are hydrocarbons containing one or more and eight or less carbon atoms. C3 to C8 hydrocarbons each may be any of a linear-chain compound, a side-chain compound, and a cyclic compound. C2 to C8 hydrocarbons each may be either a saturated hydrocarbon (i.e., the absence of a double bond and a triple bond in a molecule) or an unsaturated hydrocarbon (i.e., the presence of a double bond and/or a triple bond in a molecule). C1 to C4 may, for example, be methane ($CH_4$), ethane ($C_2H_6$), ethylene ($C_2H_4$), propane ($C_3H_8$), propylene ($C_3H_6$), normal butane ($CH_3(CH_2)_2CH_3$), isobutane ($CH(CH_3)_3$), 1-butene ($CH_2$=$CHCH_2CH_3$), 2-butene ($CH_3CH$=$CHCH_3$), or isobutene ($CH_2$=$C(CH_3)_2$).

The aforementioned organic acid may, for example, be carboxylic acid or sulfonic acid. The carboxylic acid may, for example, be formic acid ($CH_2O_2$), acetic acid ($C_2H_4O_2$), oxalic acid ($C_2H_2O_4$), acrylic acid ($C_3H_4O_2$), or benzoic acid ($C_6H_5COOH$). The sulfonic acid may, for example, be ethane sulfonic acid ($C_2H_6O_3S$). The organic acid may be either a chain compound or a cyclic compound.

The aforementioned alcohol may, for example, be methanol ($CH_3OH$), ethanol ($C_2H_5OH$), isopropanol (2-propanol) ($CH_3CH(OH)CH_3$), ethylene glycol ($CH_2(OH)CH_2(OH)$), or butanol ($C_4H_9OH$).

The mercaptans are organic compounds with terminal sulfur hydride (SH) and are substances called also thiol or thioalcohol. The aforementioned mercaptans may, for example, be methyl mercaptans ($CH_3SH$), ethyl mercaptans ($C_2H_5SH$), or 1-propane thiol ($C_3H_7SH$).

The aforementioned ester may, for example, be formic acid ester or acetic acid ester.

The aforementioned ether may, for example, be dimethyl ether (($CH_3)_2O$), methyl ethyl ether ($C_2H_5OCH_3$), or diethyl ether (($C_2H_5)_2O$).

The aforementioned ketone may, for example, be acetone (($CH_3)_2CO$), methyl ethyl ketone ($C_2H_5COCH_3$), or diethyl ketone (($C_2H_5)_2CO$).

The aforementioned aldehyde may, for example, be acetaldehyde ($CH_3CHO$), propionaldehyde ($C_2H_5CHO$), or butanal (butyraldehyde) ($C_3H_7CHO$).

The following description takes the example of the case where the mixture of substances to be separated by the separator 2 is a mixed gas including a plurality of types of gases.

The separator 2 includes the zeolite membrane complex 1, sealers 21, an outer cylinder 22, seal member 23, a supply part 26, a first collecting part 27, and a second collecting part 28. The zeolite membrane complex 1, the sealer 21, and the seal members 23 are placed in the outer cylinder 22. The supply part 26, the first collecting part 27, and the second collecting part 28 are disposed outside the outer cylinder 22 and connected to the outer cylinder 22.

The sealers 21 are members mounted on the both ends of the support 11 in the longitudinal direction (i.e., left-right direction in FIG. 6) and covering and sealing the both end faces of the support 11 in the longitudinal direction and the outside surface of the support 11 in the vicinity of the both end faces. The sealers 21 prevent the inflow and outflow of gases from the opposite generally ring-shaped both end faces of the support 11. The sealers 21 are, for example, plate-like members formed of glass or resin. The material and shape of the sealers 21 may be appropriately changed. The right sealer 21 in FIG. 6 has an opening that overlaps with the inner flow path 111 of the support 11, and therefore a right end opening of the inner flow path 111 is not covered with the sealer 21. Accordingly, the gas in the inner flow path 111 can flow out from this end opening to the outside of the zeolite membrane complex 1. On the other hand, the left sealer 21 in FIG. 6 has no opening, and therefore the gas cannot flow in and out through the left end of the inner flow path 111.

The outer cylinder 22 is a generally cylindrical tubular member. The outer cylinder 22 is formed of, for example, stainless steel or carbon steel. The longitudinal direction of the outer cylinder 22 is approximately parallel to the longitudinal direction of the zeolite membrane complex I (i.e., direction pointing in the central axis J1). The outer cylinder 22 has a supply port 221 and a first exhaust port 222 on the outside surface. The supply port 221 and the first exhaust port 222 are, for example, arranged on the opposite sides in the radial direction with the zeolite membrane complex 1 sandwiched therebetween (i.e., at 180° different positions in the circumferential direction). The outer cylinder 22 also has a second exhaust port 223 on one end in the longitudinal direction (i.e., right end in FIG. 6). The supply port 221 is connected to the supply part 26. The first exhaust port 222 is connected to the first collecting part 27. The second exhaust port 223 is connected to the second collecting part 28. An internal space of the outer cylinder 22 is an enclosed space isolated from the space around the outer cylinder 22.

The seal member 23 is arranged around the entire circumference between the outside surface of the zeolite membrane complex 1 and the inside surface of the outer cylinder 22 in the vicinity of an end of the zeolite membrane complex 1 in the longitudinal direction. The seal member 23 is a generally ring-shaped member formed of a material that is impermeable to gases. For example, the seal member 23 is O-ring formed of a resin having flexibility. The seal member 23 is in tight contact with the outside surface of the zeolite membrane complex 1 and the inside surface of the outer cylinder 22 around the entire circumference. In the example illustrated in FIG. 6, the seal member 23 is in tight contact with the outside surface of the right sealer 21 in the drawing and is indirectly in tight contact with the outside surface of the zeolite membrane complex 1 via this sealer 21. A space between the seal member 23 and the outside surface of the zeolite membrane complex 1 and a space between the seal member 23 and the inside surface of the outer cylinder 22 are sealed so as to almost or completely disable the passage of gases. Note that the seal member 23 may be provided between the outer cylinder 22 and an end face of the zeolite membrane complex 1 in the longitudinal direction.

The supply part 26 supplies a mixed gas to the internal space of the outer cylinder 22 through the supply port 221. For example, the supply part 26 is a blower or pump that transmits the mixed gas toward the outer cylinder 22 under pressure. The blower or pump includes a pressure regulator that regulates the pressure of the mixed gas supplied to the outer cylinder 22. The first collecting part 27 and the second collecting part 28 are, for example, reservoirs that store the gas derived from the outer cylinder 22, or are blowers or pumps that transfer the gas.

In the case of separating a mixed gas, the aforementioned separator 2 is provided to prepare the zeolite membrane complex 1 (step S21). Then, the supply part 26 supplies a mixed gas that includes a plurality of types of gases having different permeability to the zeolite membrane 12, to the internal space of the outer cylinder 22. For example, the mixed gas is composed predominantly of $CO_2$ and $CH_4$. The mixed gas may also include other gases different from $CO_2$ and $CH_4$. The pressure of the mixed gas supplied from the supply part 26 to the internal space of the outer cylinder 22 (i.e., supply pressure) is, for example, in the range of 0.1 MPa to 20.0 MPa. The temperature of separating the mixed gas is, for example, in the range of 10° C. to 150° C.

The mixed gas supplied from the supply part 26 to the outer cylinder 22 flows toward the outside surface of the zeolite membrane complex 1, as indicated by an arrow 251. A gas having high permeability (e.g., $CO_2$ and hereinafter referred to as a "high-permeability substance") in the mixed gas permeates through the zeolite membrane 12 provided on the outside surface 112 of the support 11 and through the support 11, and is then emitted from the inside surface 113 of the support 11 to the inner flow path 111. Accordingly, the high-permeability substance is separated from a gas having low permeability (e.g., $CH_4$ and hereinafter referred to as a "low-permeability substance") in the mixed gas (step S22). The gas emitted from the inside surface 113 of the support 11 to the inner flow path 111 (hereinafter referred to as a "permeated substance") is collected by the second collecting part 28 through the second exhaust port 223, as indicated by an arrow 253. The pressure (i.e., permeation pressure) of the gas collected by the second collecting part 28 through the second exhaust port 223 is, for example, approximately one atmospheric pressure (0.101 MPa). The permeated substance may include a substance other than the aforementioned high-permeability substance.

In the mixed gas, a gas other than the gas having permeated through the zeolite membrane 12 and the support 11 (hereinafter, referred to as a "non-permeated substance") passes through the space between the outside surface of the zeolite membrane complex 1 and the inside surface of the outer cylinder 22 from the upper side to the lower side in the drawing and is collected by the first collecting part 27 through the first exhaust port 222, as indicated by an arrow 252. The pressure of the gas collected by the first collecting part 27 through the first exhaust port 222 is, for example, approximately the same pressure as the supply pressure. The non-permeated substance may also include a high-permeability substance that has not permeated through the zeolite membrane 12, in addition to the aforementioned low-permeability substance.

As described above, the porous cylindrical support 11 used to support the zeolite membrane 12 has the generally cylindrical inside surface 113 having the central axis J1 extending in the longitudinal direction as its center, and the generally cylindrical outside surface 112 surrounding the inside surface 113. The zeolite membrane 12 is formed on the outside surface 112. The radial distance between the inside surface 113 and the outside surface 112, i.e., the maximum value A and the minimum value B in the circumferential direction of the thickness of the support, satisfy $(A-B)/(A+B) \leq 0.3$ in at least part of the support 11 in the longitudinal direction.

By reducing the variation in the support thickness in this way, as described previously, it is possible for the support 11 to improve uniformity in the membrane thickness of the zeolite membrane 12 formed on the support 11. Accordingly, even in the case where the zeolite membrane 12 is formed to a small mean thickness, it is possible to prevent part of the zeolite membrane 12 from becoming a defect by becoming too thin. As a result, the dense and thin zeolite membrane 12 can be formed on the support 11.

As described above, it is preferable for the support 11 that the maximum value A and the minimum value B of the support thickness in the circumferential direction satisfy $(A-B)/(A+B) \leq 0.3$ along the entire length of the support 11 in the longitudinal direction. This further improves uniformity in the membrane thickness of the zeolite membrane 12 formed on the support 11.

As described above, it is preferable for the support 11 that the maximum value A and the minimum value B of the support thickness in the circumferential direction satisfy (A−B)/(A+B)≤0.2, and in particular (A−B)/(A+B)≤0.1 in at least part of the support 11 in the longitudinal direction. This further improves uniformity in the membrane thickness of the zeolite membrane 12 formed on the support 11.

As described above, it is more preferable for the support 11 that the maximum value A and the minimum value B of the support thickness in the circumferential direction satisfy (A−B)/(A+B)≤0.2, and in particular (A−B)/(A+B)≤0.1, along the entire length of the support 11 in the longitudinal direction. This further improves uniformity in the membrane thickness of the zeolite membrane 12 formed on the support 11.

As described above, it is preferable for the support 11 that the mean radius X and the roundness Y of the inside surface 113 satisfy Y/X≤0.5, yet more preferably Y/X≤0.3, and in particular Y/X≤0.1, in at least part of the support 11 in the longitudinal direction. In this way, if the cross-sectional shape of the inside surface 113 perpendicular to the central axis J1 is relatively close to a perfect circle, it is possible to improve uniformity in support thickness in the circumferential direction when the outside surface 112 is made closer to a perfect circle by grinding or other methods at the time of forming the support 11. Accordingly, the support 11, at least part of which in the longitudinal direction satisfies (A−B)/(A+B)≤0.3, can be formed with high yields.

As described above, it is more preferable for the support 11 that the mean radius X and the roundness Y of the inside surface 113 satisfy Y/X≤0.5, yet more preferably Y/X≤0.3, and in particular Y/X≤0.1, along the entire length of the support 11 in the longitudinal direction. Accordingly, the support 11 that satisfies (A−B)/(A+B)≤0.3 along the entire length in the longitudinal direction can be formed with higher yields.

As described above, the support 11 is preferably formed of a ceramic sintered compact. This enables increasing the strength of bonding between the zeolite membrane 12 and the support 11 more than in the case where the support is formed of a material other than a ceramic sintered compact, and thereby enables stably supporting the zeolite membrane 12.

The zeolite membrane complex 1 includes the aforementioned support 11, and the zeolite membrane 12 formed on the outside surface 112 of the support 11. This enables providing the zeolite membrane complex 1 that includes the zeolite membrane 12 having high uniformity in membrane thickness. Accordingly, it is also possible to provide the zeolite membrane complex 1 that includes the dense and thin zeolite membrane 12. In other words, the zeolite membrane complex 1 can reduce the thickness of the zeolite membrane 12.

Since, as described above, the zeolite membrane complex 1 can reduce the thickness of the zeolite membrane 12, the structure of the zeolite membrane complex 1 is in particular suitable for use as a zeolite membrane complex that includes a zeolite membrane 12 having a thickness less than or equal to 1 μm (minimum membrane thickness).

As described above, a maximum number of membered rings in the zeolite of the zeolite membrane 12 is preferably less than or equal to 8. Accordingly, when the zeolite membrane 12 is used for the separation of a mixture of substances, it is possible to favorably achieve selective permeation of a to-be-permeated substance having a relatively small molecular diameter, such as $CO_2$, and to efficiently separate the to-be-permeated substance from the mixture of substances.

The aforementioned method of producing the zeolite membrane complex 1 includes the step of preparing seed crystals (step S12), the step of depositing the seed crystals on the support 11 (step S13), and the step of forming the zeolite membrane 12 on the support 11 by growing a zeolite from the seed crystals by hydrothermal synthesis (step S14). Accordingly, it is possible to provide the zeolite membrane complex 1 that includes the zeolite membrane 12 having high uniformity in membrane thickness. It is also possible to provide the zeolite membrane complex 1 that includes the dense and thin zeolite membrane 12.

The aforementioned separation method includes the step of preparing the above-described zeolite membrane complex 1 (step S21), and the step of supplying a mixture of substances including a plurality of types of gases or liquids to the zeolite membrane 12 and separating a substance with high permeability in the mixture of substances from the mixture of substances by causing the substance with high permeability to permeate through the zeolite membrane complex 1 (step S22). This enables favorably separating a substance with high permeability (i.e., high-permeability substance) from the mixture of substances.

This separation method is in particular suitable for use in the separation of a mixture of substances including one or more kinds of substances including hydrogen, helium, nitrogen, oxygen, water, water vapor, carbon monoxide, carbon dioxide, nitrogen oxide, ammonia, sulfur oxide, hydrogen sulfide, hydrogen fluoride, mercury, arsine, hydrocyanic acid, carbonyl sulfide, C1 to C8 hydrocarbons, organic acid, alcohol, mercaptans, ester, ether, ketone, and aldehyde.

The support 11, the zeolite membrane complex 1, the method of producing the zeolite membrane complex 1, and the separation method for a mixture of substances, described above, may be modified in various ways.

For example, the support 11 does not necessarily have to be formed of a ceramic sintered compact, and may be formed of other materials such as metal. The mean radius X and the roundness Y of the inside surface 113 of the support 11 do not necessarily have to satisfy Y/X≤0.5. The central axis of the outside surface 112 of the support 11 does not necessarily have to match the central axis J1 of the inside surface 113, and may be different from the central axis J1.

In the zeolite membrane complex 1, the membrane thickness of the zeolite membrane 12 is not limited to be less than or equal to 1 μm, and may be modified in various ways. A maximum number of membered rings in the zeolite of the zeolite membrane 12 may be greater than 8, or may be smaller than 8.

The aforementioned support 11 may be produced by a production method different from the method described in the above example. For example, the outside surface does not necessarily have to be grinded.

The aforementioned zeolite membrane complex 1 may be produced by a production method different from the method described in the above example. For example, a technique different from the technique described in the above example may be used to deposit seed crystals on the support 11. The zeolite membrane 12 may be formed on the inside surface 113 of the support 11, or may be formed on both of the outside surface 112 and the inside surface 113 of the support 11.

The structure of the separation apparatus 2 illustrated in FIG. 6 may be modified in various ways. For example, like the right sealer 21 in FIG. 6, the left sealer 21 in FIG. 6 may also have an opening that overlaps with the inner flow path 111, and seal member 23 may be provided for sealing. Also, the left end face of the outer cylinder 22 may also have a second exhaust port 223 that is connected to the second collecting part 28.

The separator 2 and the separation method described above may separate a substance other than the substance exemplified in the above description from a mixture of substances.

The zeolite membrane 12 in the zeolite membrane complex 1 does not necessarily have to be used for the separation of a high-permeability substance from a mixture of substances, and may be used in other applications such as for use as an absorption membrane or a pervaporation membrane.

The configurations of the preferred embodiments and variations described above may be appropriately combined as long as there are no mutual inconsistencies.

While the invention has been shown and described in detail, the foregoing description is in all aspects illustrative and not restrictive. It is therefore understood that numerous modifications and variations can be devised without departing from the scope of the invention.

INDUSTRIAL APPLICABILITY

The support according to the present invention is, for example, applicable for use in supporting a zeolite membrane that can be used as a gas separation membrane. The zeolite membrane complex according to the present invention is applicable in various fields that use zeolites, such as for use as a gas separation membrane, a separation membrane for substances other than gases, and an adsorption membrane for various substances.

REFERENCE SIGNS LIST

1 Zeolite membrane complex
11 Support
12 Zeolite membrane
112 Outside surface (of support)
113 Inside surface (of support)
A Maximum value (for support thickness in circumferential direction)
B Minimum value (for support thickness in circumferential direction)
J1 Central axis
S11 to S15, S21, and S22 Step

The invention claimed is:

1. A porous cylindrical support for use in supporting a zeolite membrane, comprising:
a generally cylindrical inside surface having a central axis extending in a longitudinal direction; and
a generally cylindrical outside surface that surrounds said inside surface,
wherein a maximum value A and a minimum value B of a support thickness in a circumferential direction satisfy $(A-B)/(A+B) \leq 0.3$ in at least part of the support in the longitudinal direction, the support thickness being a radial distance between said inside surface and said outside surface.

2. The support according to claim 1, wherein
said maximum value A and said minimum value B satisfy $(A-B)/(A+B) \leq 0.3$ along an entire length of the support in the longitudinal direction.

3. The support according to claim 1, wherein
said maximum value A and said minimum value B satisfy $(A-B)/(A+B) \leq 0.2$ in at least part of the support in the longitudinal direction.

4. The support according to claim 1, wherein
said inside surface has a mean radius X and roundness Y that satisfy $Y/X \leq 0.5$ in said at least part of the support in the longitudinal direction.

5. The support according to claim 1, being formed of a ceramic sintered compact.

* * * * *